United States Patent [19]

Noda et al.

[11] Patent Number: 5,536,812
[45] Date of Patent: Jul. 16, 1996

[54] CALCITONIN ANALOGUE AND USE THEREOF

[75] Inventors: Hitoshi Noda; Shigeaki Yoshina; Tsutomu Ishida; Noboru Tomiya, all of Nagoya, Japan

[73] Assignee: Sanwa Kagaku Kenkyusho Co., Ltd., Nagoya, Japan

[21] Appl. No.: 490,669

[22] Filed: Jun. 15, 1995

[30] Foreign Application Priority Data

Jun. 21, 1994 [JP] Japan ................................ 6-138618

[51] Int. Cl.$^6$ ......................... A61K 38/23; C07K 14/585
[52] U.S. Cl. ............................ 530/307; 514/808; 514/12
[58] Field of Search .............................. 530/307; 514/12, 514/2, 808

[56] References Cited

U.S. PATENT DOCUMENTS

| | | | |
|---|---|---|---|
| 4,652,627 | 3/1987 | Kempe et al. | 530/307 |
| 5,175,146 | 12/1992 | Basava et al. | 514/12 |
| 5,310,277 | 5/1994 | Lattanzi et al. | 514/12 |

FOREIGN PATENT DOCUMENTS

| | | |
|---|---|---|
| 3-80096A | 4/1991 | Japan . |
| 4-59795A | 2/1992 | Japan . |

OTHER PUBLICATIONS

"Chemistry of the Calcitonins: Species Variation Plus Structure–Activity Relations, and Pharmacologic Implications," Department of Medicine, Endocrine Unit, Mass. General Hospital and Harvard Medical School, Boston, Mass., J. T. Potts et al., pp. 121–127 (1968).

"Synthesis and Biological Activity of Peptide Sequences Related to Porcine αThyrocalcitonin," Chemistry and Immunochemistry, P. Sieber et al., pp. 28–33 (1968).

"Structure–Activity Relationship of Human Calcitonin. III. Biological Activity of Synthetic Analogues with Shortened or Terminally Modified Peptide Chains," Experientia, vol. 32, pp. 246–249 (1976), W. Rittel et al.

"Thyrocalcitonin: Hypocalcemic Hypophosphatemic Principle of the ThyroidGland," Science vol. 146, pp. 412–413 (1963), P. F. Hirsch et al.

"Calcitonin: Inhibitory Effect on Eating in Rats," Science vol. 206, pp. 850–852 (1979), W. J. Freed et al.

"Inhibition of Gastric Secretion by Calcitonin in Man," Horm. Metab. Res., vol. 3, p. 140 (1971), R. D. Hesch et al.

"Peptides From The Calcitonin Genes: Molecular Genetics, Structure & Function," Journal on Biochem., vol. 255, p. 377–390 (1988), L. H. Breimer et al.

*Primary Examiner*—Elizabeth C. Weimar
*Assistant Examiner*—Anish Gupta
*Attorney, Agent, or Firm*—Nikaido, Marmelstein, Murray & Oram

[57] ABSTRACT

The invention provides a polypeptide of calcitonin analogue and use thereof. The polypeptide has such an amino acid sequence that proline-amide residue (Pro-NH$_2$) at C-terminal of native eel calcitonin is substituted to a homoserine amide residue (Hse·NH$_2$).

3 Claims, No Drawings

SEQUENCE LISTING ( 1 ) GENERAL INFORMATION:

( i i i ) NUMBER OF SEQUENCES: 4

( 2 ) INFORMATION FOR SEQ ID NO: 1 :

( i ) SEQUENCE CHARACTERISTICS:
( A ) LENGTH: 32 Amino acids
( B ) TYPE: Amino acid
( C ) STRANDEDNESS: Single
( D ) TOPOLOGY: Both ( i i ) MOLECULE TYPE: Peptide ( i i i ) HYPOTHETICAL: No ( i v ) ANTI-SENSE: No ( x i ) SEQUENCE DESCRIPTION: SEQ ID NO : 1 :

Cys Gly Asn Leu Ser Thr Cys Met Leu Gly Thr Tyr Thr Gln Asp Phe Asn
              5                   10                  15

Lys Phe His Thr Phe Pro Gln Thr Ala Ile Gly Val Gly Ala Pro
            20                  25                  30

( 2 ) INFORMATION FOR SEQ ID NO: 2 :

( i ) SEQUENCE CHARACTERISTICS:
        ( A ) LENGTH: 32 Amino acids
        ( B ) TYPE: Amino acid
        ( C ) STRANDEDNESS: Single
        ( D ) TOPOLOGY: Both ( i i ) MOLECULE TYPE: Peptide ( i i i ) HYPOTHETICAL: No ( i v ) ANTI-SENSE: No ( x i ) SEQUENCE DESCRIPTION: SEQ ID NO : 2 :

Cys Ser Asn Leu Ser Thr Cys Val Leu Gly Lys Leu Ser Gln Glu Leu His
              5                   10                  15

Lys Leu Gln Thr Tyr Pro Arg Thr Asp Val Gly Ala Gly Thr Xaa
            20                  25                  30

( 2 ) INFORMATION FOR SEQ ID NO: 3 :

( i ) SEQUENCE CHARACTERISTICS:
        ( A ) LENGTH: 32 Amino acids
        ( B ) TYPE: Amino acid
        ( C ) STRANDEDNESS: Single
        ( D ) TOPOLOGY: Linear ( i i ) MOLECULE TYPE: Peptide ( i i i ) HYPOTHETICAL: No ( i v ) ANTI-SENSE: No ( x i ) SEQUENCE DESCRIPTION: SEQ ID NO : 3 :

Cys Ser Asn Leu Ser Thr Cys Val Leu Gly Lys Leu Ser Gln Glu Leu His
              5                   10                  15

Lys Leu Gln Thr Tyr Pro Arg Thr Asp Val Gly Ala Gly Thr Pro
            20                  25                  30

( 2 ) INFORMATION FOR SEQ ID NO: 4 :

( i ) SEQUENCE CHARACTERISTICS:
        ( A ) LENGTH: 32 Amino acids
        ( B ) TYPE: Amino acid
        ( C ) STRANDEDNESS: Single
        ( D ) TOPOLOGY: Linear ( i i ) MOLECULE TYPE: Peptide ( i i i ) HYPOTHETICAL: No ( i v ) ANTI-SENSE: No ( x i ) SEQUENCE DESCRIPTION: SEQ ID NO : 4 :

Cys Ser Asn Leu Ser Thr Cys Val Leu Gly Lys Leu Ser Gln Glu Leu His
              5                   10                  15

Lys Leu Gln Thr Tyr Pro Arg Thr Asp Val Gly Ala Gly Thr Xaa
            20                  25                  30

CALCITONIN ANALOGUE AND USE THEREOF

BACKGROUND OF THE INVENTION (1) Field of the invention

The invention relates to a polypeptide of calcitonin analogue and use thereof.

The polypeptide can be used to prevent and/or cure calcium metabolic diseases such as reduction of ache in osteoporosis, prevention of fracture in osteogenesis imperfecta, and curing of hypercalcemia and Paget's disease.

(2) Related arts

Calcitonin was firstly found by D. H. Copp et al. in the year of 1961 from human jugular vein blood as one of peptide hormones, which shows an activity of reducing a calcium concentration in blood.

The calcitonin has been constructed from 32 amino acid residues having a sequence (substantially corresponding to SEQ ID NO: 1), as shown below.

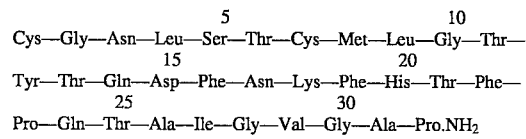

In the amino acid sequence, Pro·NH$_2$ means proline amide residue and Cys residues in the 1st and 7th positions are linked by a disulfide bond.

Thereafter, peptide hormones having biological activities similar to the calcitonin have been extracted from various animals such as salmon, eel, chicken, pig, rat, sheep, cow, rabbit and stingray, and amino acid sequences of such native calcitonins have been determined.

Structural features of calcitonins include a constant chain length of 32 amino acids, a disulfide bridge between the cysteine residues in positions 1 and 7, forming a ring of seven amino acid residues at the N-terminal, and a carboxy terminal proline amide. However, amino acid residues common to all calcitonins are those in 1, 4th–7th, 28th and 32nd positions, only (7 amino acid residues in total). It has been considered that the proline amide at C-terminal, common to all calcitonins, is indispensable for developing biological activities thereof [J. T. Potts, Jr. et al., "Calcium, Parathyroid Hormone and the Calcitonins", page 121 printed by Excerpta Medica, Amsterdam (1971); P. Sieber, "Calcitonin 1969", page 28, Proc. 2nd Symp., printed by Medical Books, London (1970); and W. Rittel et al., "Experientia", Vol. 32, page 246 (1976)].

It has been known that the calcitonins show biological activities of reducing calcium concentration in blood [P. F. Hirsch et al., "Science", Vol. 146, page 412 (1963)], inhibition of feeding [W. J. Freed et al., "Science", Vol. 206, page 850 (1979)], and inhibition of gastric secretion [R. D. Hesch et al., "Horm. Metab. Res.", Vol. 3, page 140 (1971)].

For obtaining the calcitonins, extraction from mammalian blood and tissue samples was firstly tried and then chemical synthesis has been employed. The former has disadvantages of limitation from availability of the raw material and troublesome in purifying operations, and the latter has also disadvantages of that synthetic operations are troublesome, since all of calcitonins are constructed from 32 amino acid residues, and that long period of time is required for synthesis per se and purification, so that it has been quite difficult to provide the calcitonins in a large amount with reasonable cost.

In the recent years, the genetic engineering has remarkably developed and such a process utilizing techniques in the genetic engineering has been proposed, which comprises steps of synthesizing a single-stranded DNA fragment encoding one of calcitonins by using a DNA synthesizer and its single-stranded cDNA, preparing a double-stranded DNA fragment from the single-stranded DNA fragments, purifying the double-stranded DNA fragment, inserting the purified double-stranded DNA fragment into a vector, transforming Escherichia coli by the recombinant vector, cultivating the transformant to express a polypeptide encoding the calcitonin, and separating and purifying the expressed polypeptide. In this case, however, a polypeptide with a C-terminal proline amide and showing the desired biological activities can not be expressed by Escherichia coli and thus the C-terminal amidating treatment is required during the separating-purifying step, but a C-terminal amidating enzyme is expensive, the enzymatic treatment requires special techniques and a skill, and the enzymatic process makes yield of the objective substance low. Therefore, this conventional process can not be said as one suitable for industrial scale production of calcitonins, from view points of cost on the reagent and yield.

Therefore, researchers in the assignee company have energetically studied and investigated on a process utilizing genetic recombination techniques to find that various calcitonin analogues can be obtained without use of the expensive C-terminal amidating enzyme, each of which analogues includes no methionine residue (Met) in its amino acid sequence thereof and C-terminal structure is proline$^{32}$-homoserine$^{33}$ amide (Pro$^{32}$-Hse$^{33}$-NH$_2$), a primary alkyl, 1–20 carbon atoms, amide of homoserine$^{33}$, or an optional polypeptide chain and containing homoserine amide at C-terminal [Jap. Pat. Hei 4 (A. D. 1992) - 59795(A) which corresponds to EP-A-0 464 549]. The process described in these patent literatures is somewhat similar to a process proposed by the assignee company on motilin analogues as one of peptide hormones and disclosed in Jap. Pat. Hei 3 (A.D. 1991) - 80096(A) which corresponds to EP-A-0 355 720. Namely, according to the process described in the patent literatures, each of the calcitonin analogues can be prepared by synthesizing a single-stranded DNA fragment consisting of a leader polypeptide at N-terminus and with Met residue at its C-terminus, a polypeptide encoding the calcitonin analogue gene and with Met residue at its C-terminus, a spacer peptide with Met residue at its C-terminus, a polypeptide encoding the calcitonin analogue gene with Met residue at its C-terminus (the spacer peptide and calcitonin analogue gene being arranged in plural); synthesizing a single-stranded DNA fragment complementary to the first single-stranded DNA fragment; preparing a double-stranded DNA fragment by the single-stranded fragments; inserting the double-stranded fragment into a vector such as a plasmid to obtain a recombinant vector; transforming by the recombinant vector a microorganism such as Escherichia coli or mammalian cell such as CttO cell; cultivating the transformant to express the polypeptide as an inclusion body or fused protein in the transformant; treating the inclusion body with cyanogen bromide to cleave at each position of Met and modify the amino acid residue of Met at C-terminal into Hse or Hse-lactone residue; treating the reaction solution with an acid, for instance 0.1N HCl solution (at 30° C. for 3 hours) to convert all of individual polypeptides into those with Hse-lactone residue at C-terminus; lyophilizing the same; and then treating the same with ammonia solution or reacted with a primary alkyl amine.

The method disclosed in said patent literatures makes possible the preparation of various calcitonin analogues in a large amount and with reasonable cost, but a biological activities of those, for instance salmon I calcitonin-Hse$^{33}$-NH$_2$ is substantially same with the native Salmon I calcitonin.

SUMMARY OF THE INVENTION

One of the objects of the invention is to provide a calcitonin analogue which is excellent in productivity as in said patent literatures and shows remarkably higher biological activities than its basic native type calcitonin.

An additional but important object of the invention is to provide a pharmaceutical composition for preventing and/or curing calcium metabolic diseases, which contains the calcitonin analogue as an effective ingredient.

DETAILED DESCRIPTION OF THE INVENTION

The inventors have energetically studied and discovered that a substitution of Pro$^{32}$-NH$_2$ at the C-terminal by Hse$_{32}$-NH2 remarkably enhances the biological activities, although the structure of the C-terminal Pro-NH$_2$ common to all of native calcitonins has been considered as essential for developing the biological activities thereof, so that the invention was established.

The calcitonin analogue according to the invention is, therefore, characterized in that an amino acid sequence (substantially corresponding to SEQ ID NO: 2) thereof is

```
                     5                      10
    Cys—Ser—Asn—Leu—Ser—Thr—Cys—Val—Leu—Gly—Lys—
                    15                     20
    Leu—Ser—Gln—Glu—Leu—His—Lys—Leu—Gln—Thr—Tyr—
                    25                     30
    Pro—Arg—Thr—Asp—Val—Gly—Ala—Gly—Thr—Hse.NH₂
```

In the amino acid sequence, Hse·NH$_2$ means homoserine amide and Cys residues in the 1st and 7th positions 1 and 7 are linked by a disulfide bond.

The amino acid sequence is same with that for eel calcitonin excepting that the amino acid residue at C-terminal in the latter is Pro·NH$_2$.

The pharmaceutical composition according to the invention and for preventing and/or curing calcium metabolic diseases is characterized by containing as an effective ingredient the calcitonin analogue having said amino acid sequence.

The calcitonin analogue according to the invention can be prepared by synthesizing by a peptide synthesizer a polypeptide encoding said amino acid sequence but having rise residue at the 32nd position, oxidizing thiol group in Cys at 1st and 7th positions by potassium ferricyanide to yield a disulfide linkage between two Cys residues, treating the polypeptide with an acid to form a polypeptide having Hse-lactone residue at C-terminal, and treating the polypeptide with an ammonia to amidate C-terminal thereof.

For obtaining the calcitonin analogue in a large amount, the techniques as disclosed in said Jap. Pat. Hei 3 (A.D. 1991) - 80096(A) corresponding to EP-A-0 355 720 have been utilized. Namely, the calcitonin analogue is prepared by synthesizing a single-stranded DNA fragment consisting of a leader polypeptide at N-terminus and with Met residue at its C-terminus, a polypeptide encoding the calcitonin analogue gene and with Met residue at its C-terminal of the 32nd position, a spacer peptide with Met residue at its C-terminus, a polypeptide encoding the calcitonin analogue gene with Met residue at its C-terminal (the spacer peptide and calcitonin analogue gene being arranged in plural); synthesizing a single-stranded DNA fragment complementary to the first single-stranded fragment; preparing a double-stranded DNA fragment by the single-stranded fragments; inserting the double-stranded fragment into a vector such as a plasmid to obtain a recombinant vector; transforming by the recombinant vector a microorganism such as *Escherichia coli* or mammalian cell such as CHO cell; cultivating the transformant to express a protein as an inclusion body or fused protein in the transformant; treating the inclusion body with cyanogen bromide to cause a cleavage at each position of Met and modify the amino acid residue of Met at C-terminus into Hse or Hse-lactone residue; and then treating the reaction solution with the potassium ferricyanide, acid and ammonia, as referred to above.

DETAILED DESCRIPTION OF PREFERRED EMBODIMENTS

The invention will now be further explained with reference to a Reference Example, Example, Biological Test Example and Medicine Preparation Example.

Reference Example (Synthesis of native type eel calcitonin)

A polypeptide having following amino acid sequence (corresponding to SEQ ID NO: 3) was synthesized by a peptide synthesizer (Mode 431A manufactured by Applied Biosystems Co.), and then removals of protective groups and cleavage of the linkage between the polypeptide and resin peptide was carried out by trifluoromethanesulfonic acid (TFMSA) procedure. In the synthesis, methylbenzhydrylamine resin was employed to provide a C-terminal amide peptide.

Cys-Set-Asn-Leu-Ser-Thr-Cys-Val-Leu-Gly-Lys-Leu-Ser-Gln-Glu-Leu -His-Lys-Leu-Gln-Thr-Tyr-Pro-Arg-Thr-Asp-Val-Gly-Ala-Gly-Thr -Pro

The synthesized polypeptide was purified by reverse phase high performance liquid chromatography (rp-HPLC) by using μ-bondasphere (Trademark of Waters Co.) C-18 column (19×150 mm), under following conditions and fraction in a main peak was recovered and lyophilized.

Elute: Linear gradient of 20–40% acetonitrile in 0.012N HCl (45 minutes)

Flow rate: 7.0 ml/min.

Detection wave length: 220 nm

A part (60 mg) of the lyophilized polypeptide was taken to dissolve the same in 0.05% acetic acid solution (60 ml). After adjusted pH of the solution to 8.5 by 3M aqueous ammonia solution, 0.1M potassium ferricyanide (1.8ml) was added and the mixture was stirred for 30 minutes at room temperature to form a disulfide bridge between the Cys residues in positions 1 and 7. The reaction solution adjusted its pit to 5.0 by adding 50% acetic acid solution was subjected to gel-filtration using a Sephadex (Trademark of Pharmacia AB) G-15 column to remove excess potassium ferricyanide, and then a peptide fraction was lyophilized.

The resulting lyophilized polypeptlde was subjected again to HPLC under the same conditions as above by using the μ-bondasphere (Trademark of Waters Co.) C-18 column (19×150 mm) to obtain a desired natlye type eel calcitonin.

Identification of the polypeptlde was carried out by FAB-MS analysis to confirm that the polypeptide was rightly synthesized.

Example (Synthesis of [Hse$^{33}$-NH$_2$] eel calcitonin)

A polypeptide having following amino acid sequence (corresponding to SEQ ID NO: 4) was synthesized by a peptide synthesizer (Model 431A manufactured by Applied Biosystems Co.), and then removals of protective groups and cleavage of the linkage between the polypeptide and resin peptide was carried out by TFMSA procedure. In the synthesis, aminomethylated polystyrene·HCl resin was employed and N-Boc-0-benzyl-L-homoseryl-4-(oxymethyl)phenylacetic acid was employed as Hse source (Boc: tert-butyloxycarbonyl).

Cys-Ser-Asn-Leu-Ser-Thr-Cys-Val-Leu-GlY-Lys-Leu-Ser-Gln-Glu-Leu -His-Lys-Leu-Gln-Thr-Tyr-Pro-Arg-Thr-AsP-Val-Gly-Ala-Gly-Thr -Hse·OH

The synthesized polypeptide was purified by HPLC [Waters μ-bondasphere C-18 column (19×150 mm)], under following conditions and fraction in a main peak was recovered and lyophilized.

Elute: Linear gradient of 20–40% acetonitrile in 0.012N HCl (45 minutes)

Flow rate: 7.0 ml/min.

Detection wave length: 220 nm

A part (60 mg) of the lyophilized polypeptide was taken to dissolve the same in 0.05% acetic acid solution (60 ml). After adjusted pH of the solution to 8.5 by 3M aqueous ammonia solution, 0.1M potassium ferricyanide (1.8 ml) was added and the mixture was stirred for 30 minutes at room temperature to form a disulfide bridge between the Cys residues in positions 1 and 7. The reaction solution adjusted its pH to 5.0 by adding 50% acetic acid solution was subjected to gel-filtration using a Sephadex (Trademark of Pharmacia AB) G-15 column to remove excess potassium ferricyanide, and then a peptide fraction was lyophilized.

The resulting lyophilized polypeptide was purified by reverse phase HPLC under the same conditions as above. The purified polypeptide having a C-terminal Hse residue was lyophilized and lactonized by treating in 0.1N HCl at 30° C. for 3 hours and lyophilized.

An ammonia solution (manufactured by Adrich Co., 2.0M solution in methanol) was added to the lyophilized polypeptide by 0.5 ml per 1 g of the polypeptide to stir for 1 hour at 37° C. to convert the Hse-lactone to the corresponding primary amide and then dried in vacuo to obtain a desired [Hse$^{32}$-NH$_2$]-eel calcitonin.

Identification of the polypeptide was carried out by FAB-MS analysis to confirm that the polypeptide was rightly synthesized.

Pharmacological Test Example (Measurement of biological activity)

A solution of the polypeptide obtained by each of the Example and Reference Example in 1% sodium acetate buffer (pH 4) containing 0.1% bovine serum albumin (BSA) was administered to a Wister male rat (age of 6 weeks and fasted from the previous day) from its jugular vein. Serum calcium concentration at 1 hour after the administration was measured by the OCPC method using a marketed measuring kit ("Calcium C-Test Wako" manufacture by Wako Pure pharmaceuticals Co., Ltd., Japan). Activity of sample calcitonins expressed in unit numbers were obtained by using an eel calcitonin (manufactured by Penisula Lab. Inc., Lot No. 015405, 4500 IU/mg) as a standard and 2—2 parallel dose examination method. The activity unit numbers of each sample polypeptide per 1 mg was obtained as a specific activity.

Results are shown in following Table 1. As apparently seen therefrom, it has been found that the biological activity of the calcitonin analogue according to the invention ([Hse$^{32}$-NH$_2$]-eel calcitonin) is remarkably higher than the native type eel calcitonin, wherein the 32nd amino acid is Pro-NH$_2$.

TABLE 1

| Sample | Specific activity (IU/mg) |
|---|---|
| Reference Example | 4500 |
| Example | 6800 |

Medicine Preparation Example

A solution of the calcitonin analogue (100 IU) obtained by the Example and in refined water was aseptically charged into vials. After lyophilized, the vial was sealed to obtain a dry powdery medicine. The powdery medicine is dissolved in saline or the like for injection purpose, when it shall be used.

The activity unit of the calcitonin analogue in a medicine can be changed in a range of about 10–about 200 IU.

An additive or stabilizer widely accepted for peptide hormone preparations, such as serum albumin or the like peptide and a protein can be added to the solution of calcitonin analogue.

What is claimed is:

1. A calcitonin analogue having an amino acid sequence according to SEQ ID NO: 2

```
            5                    10
Cys—Ser—Asn—Leu—Ser—Thr—Cys—Val—Leu—Gly—Lys—
           15                    20
Leu—Ser—Gln—Glu—Leu—His—Lys—Leu—Gln—Thr—Tyr—
           25                    30
Pro—Arg—Thr—Asp—Val—Gly—Ala—Gly—Thr—Hse.NH₂
``` wherein Hse·NH₂ means homoserine amide residue and Cys residues in the 1st and 7th positions are linked by a disulfide bond.

2. A pharmaceutical composition for decreasing calcium concentration in blood, comprising an effective amount of a calcitonin analogue with an amino acid sequence according to SEQ ID NO: 2

```
            5                    10
Cys—Ser—Asn—Leu—Ser—Thr—Cys—Val—Leu—Gly—Lys—
           15                    20
Leu—Ser—Gln—Glu—Leu—His—Lys—Leu—Gln—Thr—Tyr—
           25                    30
Pro—Arg—Thr—Asp—Val—Gly—Ala—Gly—Thr—Hse.NH²
``` wherein Hse·NH₂ means homoserine amide residue and Cys residues in the 1st and 7th positions are linked by a disulfide bond, in association with a nontoxic pharmaceutical carrier or excipient.

3. A method of decreasing calcium concentration in blood, comprising administering to a patient in need of such treatment an effective amount of a calcitonin analogue with an amino acid sequence according to SEQ ID NO: 2

```
            5                    10
Cys—Ser—Asn—Leu—Ser—Thr—Cys—Val—Leu—Gly—Lys—
           15                    20
Leu—Ser—Gln—Glu—Leu—His—Lys—Leu—Gln—Thr—Tyr—
           25                    30
Pro—Arg—Thr—Asp—Val—Gly—Ala—Gly—Thr—Hse.NH²
``` wherein Hse·NH₂ means homoserine amide residue and Cys residues in the 1st and 7th positions are linked by a disulfide bond, in association with a nontoxic pharmaceutical carrier or excipient.

* * * * *